(12) United States Patent
Wales et al.

(10) Patent No.: US 12,733,795 B2
(45) Date of Patent: Sep. 15, 2026

(54) AIR/WATER CONNECTOR TO PREVENT WATER LEAKING

(71) Applicant: Boston Scientific Scimed, Inc., Maple Grove, MN (US)

(72) Inventors: Ryan V. Wales, Northborough, MA (US); John B. Golden, Norton, MA (US); Jeff Gray, Sudbury, MA (US); Scott E. Brechbiel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 227 days.

(21) Appl. No.: 18/525,145

(22) Filed: Nov. 30, 2023

(65) Prior Publication Data

US 2024/0172924 A1 May 30, 2024

Related U.S. Application Data

(60) Provisional application No. 63/428,881, filed on Nov. 30, 2022.

(51) Int. Cl.
*A61B 1/00* (2006.01)

(52) U.S. Cl.
CPC ...... *A61B 1/00128* (2013.01); *A61B 1/00119* (2013.01)

(58) Field of Classification Search
CPC ........................ A61B 1/00119; A61B 1/00128
See application file for complete search history.

(56) References Cited

U.S. PATENT DOCUMENTS

| | | | | |
|---|---|---|---|---|
| 4,748,970 | A * | 6/1988 | Nakajima .......... | A61B 1/00068 600/113 |
| 5,879,288 | A * | 3/1999 | Suzuki ............... | A61B 1/00124 600/176 |
| 8,679,074 | B2 | 3/2014 | Daly et al. | |
| 9,144,373 | B2 | 9/2015 | Kaye et al. | |
| 9,560,954 | B2 | 2/2017 | Jacobs et al. | |
| 11,160,440 | B2 | 11/2021 | Briggs | |
| 11,576,566 | B2 | 2/2023 | Pollock et al. | |
| 2007/0055107 | A1 | 3/2007 | Wenchell | |
| 2009/0082634 | A1 | 3/2009 | Kathrani et al. | |

(Continued)

FOREIGN PATENT DOCUMENTS

| | | |
|---|---|---|
| CN | 212407169 U | 1/2021 |
| CN | 212407619 U | 1/2021 |

(Continued)

OTHER PUBLICATIONS

International Search Report and Written Opinion dated Mar. 1, 2024 for International Application No. PCT/US2023/081863.

*Primary Examiner* — Aaron B Fairchild
(74) *Attorney, Agent, or Firm* — Seager, Tufte & Wickhem, LLP

(57) ABSTRACT

Methods and systems for controlling leaks from a tubing set of an endoscope system during equipment changeouts. An illustrative connector arranged and configured to couple a tube set to an endoscope may comprise a housing comprising a first fluid inlet, a second fluid inlet, a first fluid outlet in selective fluid communication with the first fluid inlet, a second fluid outlet in fluid communication with the second fluid inlet, and a flow control mechanism configured to selectively fluidly couple the first fluid outlet with the first fluid inlet.

15 Claims, 11 Drawing Sheets

(56) References Cited

U.S. PATENT DOCUMENTS

| | | | |
|---|---|---|---|
| 2011/0054256 | A1 | 3/2011 | Cushner et al. |
| 2012/0095391 | A1 | 4/2012 | Bendele et al. |
| 2014/0180219 | A1 | 6/2014 | Ho et al. |
| 2016/0146359 | A1 | 5/2016 | Ferguson |
| 2019/0350440 | A1 | 11/2019 | Leong et al. |
| 2022/0192479 | A1 | 6/2022 | Harris et al. |

FOREIGN PATENT DOCUMENTS

| | | | |
|---|---|---|---|
| WO | 2022060903 | A1 | 3/2022 |
| WO | 2022140449 | A1 | 6/2022 |

* cited by examiner 500
506
534
512
542c
542a
522
536
508
544
510
502
518
520
532
516
530
504

AIR/WATER CONNECTOR TO PREVENT WATER LEAKING

CROSS-REFERENCE TO RELATED APPLICATIONS

This application claims the benefit of U.S. Provisional Patent Application Ser. No. 63/428,881 filed on Nov. 30, 2022, the disclosure of which is incorporated herein by reference.

FIELD

This disclosure relates generally to medical fluid containers and methods, and particularly to a container and tube sets to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. For example, sterile water may be used to irrigate the working lumen during the procedure. Further, during endoscopic procedures, the video lens at the distal end of the endoscope, which is used to navigate and visualize target tissues, may be prone to becoming fouled with blood, mucous, and other debris during the procedure.

The tube set used for providing irrigation fluid and/or lens wash fluid may be commonly used for a period of 24 hours across multiple endoscopic procedures. However, the same endoscope is not used for multiple patients and must be switched out between procedures. During the time the tube set connector connecting the fluid tubes to the endoscope is disconnected from the endoscope and needs to be placed somewhere. In some cases, the connector is placed in a position that tends to leak water. This may cause the floor to become wet, which may present a hazard in the procedure suite that needs to be cleaned up.

Current solutions to leaking tube sets/connectors may be to place a clip or clamp on the tube set to prevent leaks. However, this is an extra step for the nurses, technicians, or other staff which may be forgotten or add additional time between procedures. An automated or semi-automated means of preventing water from leaking out of the connector between procedures may be desirable. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example a connector arranged and configured to couple a tube set to an endoscope may comprise a housing, the housing comprising, a first fluid inlet, a second fluid inlet, a first fluid outlet in selective fluid communication with the first fluid inlet, a second fluid outlet in fluid communication with the second fluid inlet, and a flow control mechanism configured to selectively fluidly couple the first fluid outlet with the first fluid inlet.

Alternatively or additionally to any of the examples above, in another example, the flow control mechanism may comprise a septum.

Alternatively or additionally to any of the examples above, in another example, the septum may comprise a though hole extending through a thickness thereof.

Alternatively or additionally to any of the examples above, in another example, the flow control mechanism may comprise a valve.

Alternatively or additionally to any of the examples above, in another example, the valve may be a duckbill valve.

Alternatively or additionally to any of the examples above, in another example, the flow control mechanism may be over molded with the housing.

Alternatively or additionally to any of the examples above, in another example, the flow control mechanism may be configured to open at a predetermined minimum pressure.

Alternatively or additionally to any of the examples above, in another example, the valve may comprise an iris valve.

Alternatively or additionally to any of the examples above, in another example, the iris valve may be configured to open when the connector is connected to an endoscope and close when the connector is disconnected from the endoscope.

Alternatively or additionally to any of the examples above, in another example, the flow control mechanism may comprise a spring-loaded cap.

Alternatively or additionally to any of the examples above, in another example, the flow control mechanism may comprise a slidable cam and sealing member.

Alternatively or additionally to any of the examples above, in another example, when the slidable cam is in a first configuration, the sealing member may fluidly isolate the first fluid outlet from the first fluid inlet and when the slidable cam is in a second configuration, the first fluid outlet may be in fluid communication with the first fluid inlet.

In another example, a connector arranged and configured to couple a tube set to an endoscope may comprise a first housing, the first housing may comprise a first fluid inlet, a second fluid inlet, a first fluid outlet in fluid communication with the first fluid inlet, and a second fluid outlet in fluid communication with the second fluid inlet. The connector may further comprise a second housing, the second housing may comprise a third fluid inlet, a fourth fluid inlet, a third fluid outlet in selective fluid communication with the third fluid inlet, and a fourth fluid outlet in fluid communication with the fourth fluid inlet. The first housing and the second housing may be movable relative to one another to selectively couple the first and second fluid outlets of the first housing with the third and fourth fluid inlets of the second housing.

Alternatively or additionally to any of the examples above, in another example, when the first housing and the second housing are in a first configuration, the first and second fluid outlets of the first housing may be fluidly coupled with third and fourth fluid inlets of the second housing.

Alternatively or additionally to any of the examples above, in another example, when the first housing and the second housing are in a second configuration, the first and second fluid outlets of the first housing may be fluidly isolated from the third and fourth fluid inlets of the second housing.

Alternatively or additionally to any of the examples above, in another example, the first housing may further comprise a protrusion configured to selectively engage the third fluid inlet when the first housing and the second housing are in the first configuration and to selectively engage a mating recess of the second housing when the first housing and the second housing are in the second configuration.

Alternatively or additionally to any of the examples above, in another example, the second housing may further comprise a protrusion configured to selectively engage the first fluid outlet when the first housing and the second housing are in the first configuration.

In another example, a connector arranged and configured to couple a tube set to an endoscope may comprise a housing, the housing may comprise a first fluid inlet, a second fluid inlet, a first fluid outlet in selective fluid communication with the first fluid inlet, a second fluid outlet in fluid communication with the second fluid inlet, and a flow control mechanism configured to selectively fluidly couple the first fluid outlet with the first fluid inlet. The first and second fluid outlets may be configured to be coupled to an endoscope and when the first and second fluid outlets are uncoupled from the endoscope the flow control mechanism is configured to fluidly isolate the first fluid outlet from the first fluid inlet.

Alternatively or additionally to any of the examples above, in another example, the flow control mechanism may be configured to selectively open at a predetermined minimum pressure.

Alternatively or additionally to any of the examples above, in another example, the flow control mechanism may be configured to selectively open upon coupling of the connector with the endoscope.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
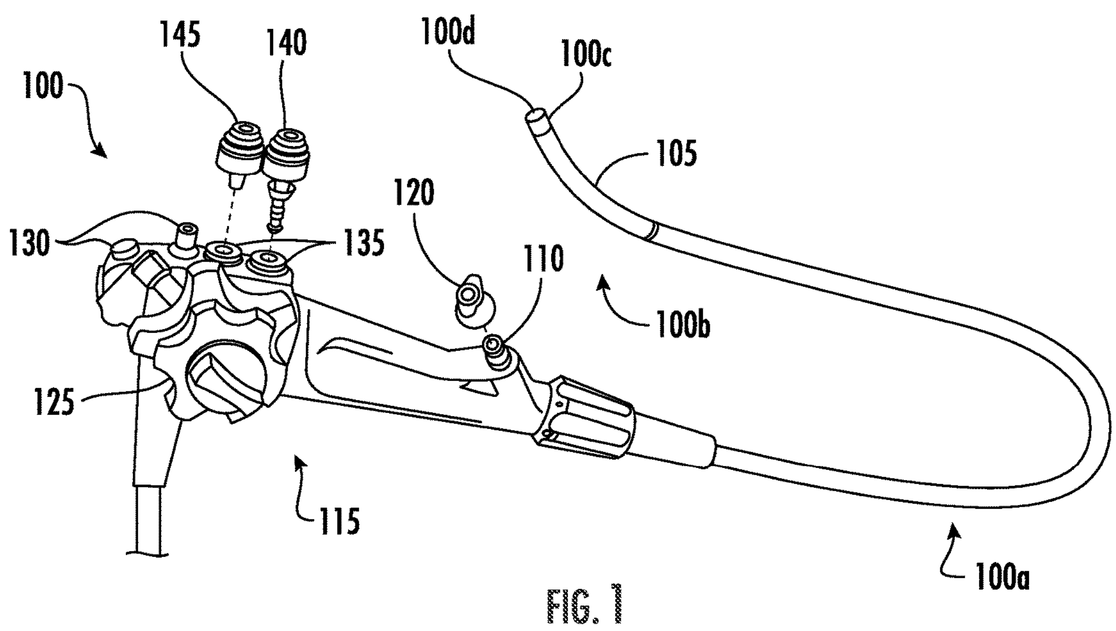
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. Some systems may use two separate water bottles for irrigation and lens wash while other systems may use a single water bottle for both irrigation and lens wash. As clinicians work through each case, some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle.

Additionally, having the sterile water bottles stowed on lower shelves of the carts, alongside the peristaltic pump, and other equipment may make these difficult to visualize and often, the clinician may not realize that the bottle is nearing empty until they are no longer able to deliver irrigation or lens wash to through the distal end of the scope. There is also an inherent risk associated with stowing the water bottles adjacent to the endoscope control boxes. For example, if the water bottle fails in some way (e.g., leak, burst, rupture, etc.) there may be a high risk of water running or spraying onto these high-cost control systems resulting in significant damage or destruction. Disclosed herein are containers and tube sets that are easily viewed by the clinician and reduces the risk of containers to the tubes when the container is replaced.

Figure 2:
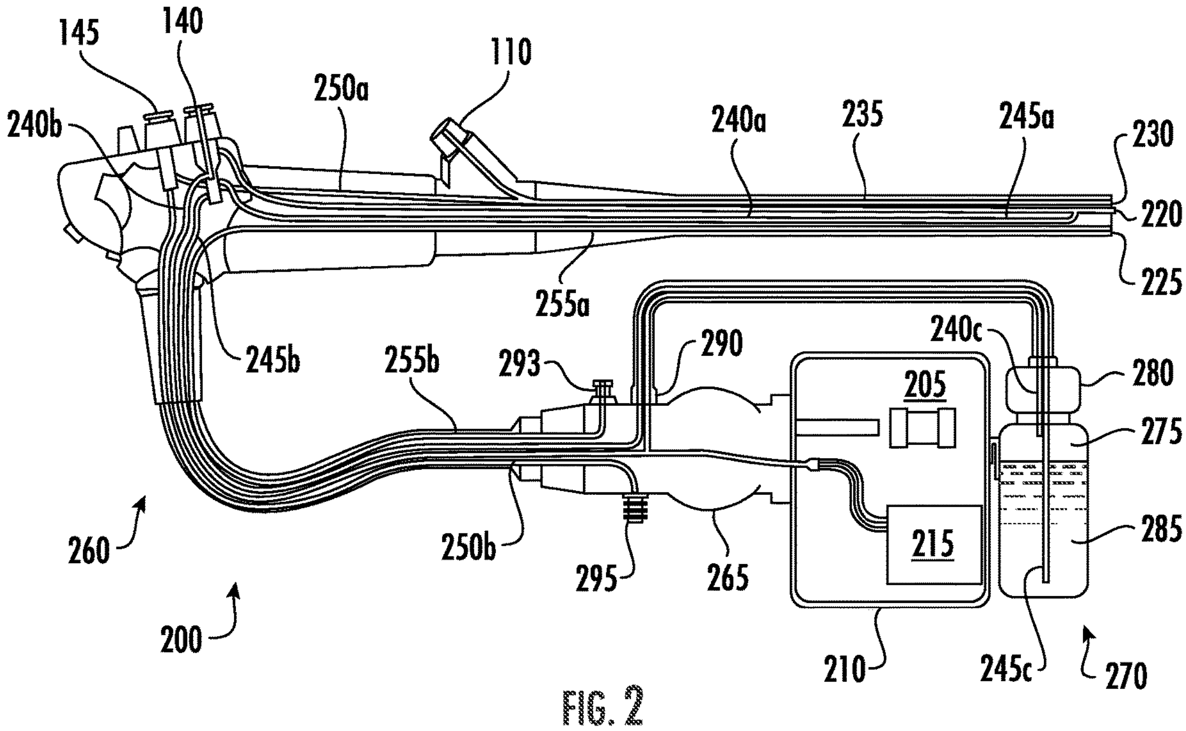
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$)

feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash supply tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash supply tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve 140 in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash supply tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash supply tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash supply tubing 245*c*, may be placed in the path of the irrigation supply tubing to help prevent backflow into the reservoir after water has passed the valve. In some cases, irrigation water may be supplied from the water reservoir 270. Some illustrative systems where the supply tubing for irrigation and lens wash are connected to and drawn from a single water reservoir are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference.

Figure 3:
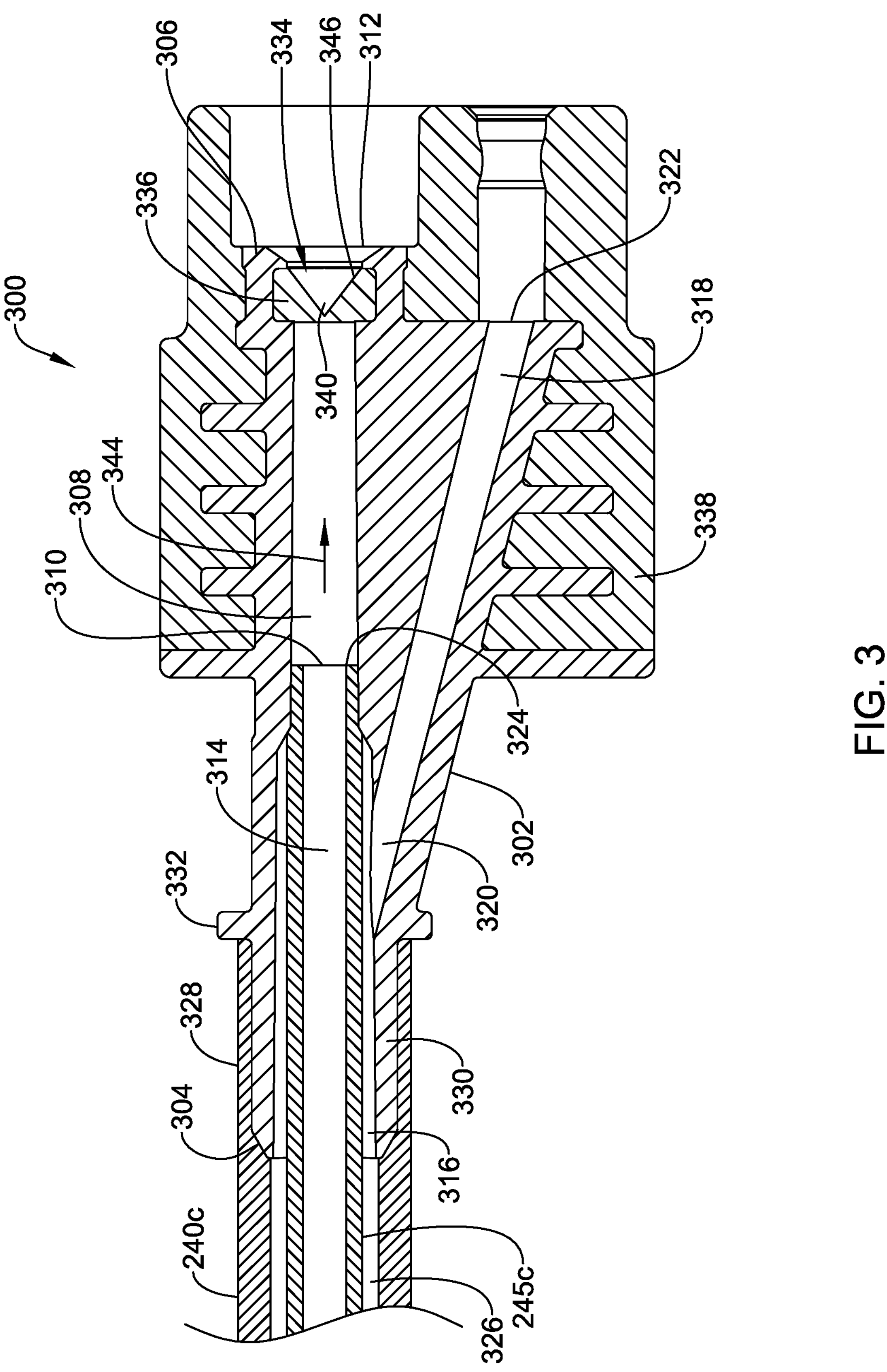
FIG. 3 depicts a cross-sectional view of an illustrative connector for connecting an endoscope end of the gas/lens wash supply tubing to the gas/lens wash connector on the connector portion.

In some cases, it may be desirable to prevent water/fluid from leaking out of the gas/lens wash supply tubing 240*c*, 245*c* (e.g., configured to be connected to gas/lens wash connector 290) and/or the irrigation tubing (not explicitly shown) (e.g., configured to be connected to the irrigation connector 293). While the illustrative connectors are described with respect to the gas/lens wash supply tubing 240*c*, 245*c*, it should be understood that the connectors and coupling configurations described herein may be used at other connection points, as desired. FIG. 3 depicts a cross-sectional view of an illustrative connector 300 for connecting an endoscope end of the gas/lens wash supply tubing 240*c*, 245*c* to the gas/lens wash connector 290 on the connector portion 265.

The connector 300 may include a housing 302 extending from a first inlet end 304 to a second outlet end 306. The first inlet end 304 may be configured to be coupled to the gas supply tubing 240*c* and the lens wash supply tubing 245*c* and the second outlet end 306 may be configured to be coupled to the gas/lens wash connector 290 on the connector portion 265. The gas supply tubing 240*c* and lens wash supply tubing 245*c* may be combined in a coaxial arrangement. For example, the gas supply tubing 240*c* may define a lumen 326 that is sufficiently large in diameter to encompass a smaller diameter lens wash supply tubing 245*c*, coaxially received within the gas supply tubing 240*c*, as well as provide air to the water source in an annular space surrounding the lens wash supply tubing 245*c* to pressurize the water reservoir. The lens wash supply tubing 245*c* may be configured to exit the lumen 326 defined by the coaxial gas supply tubing 240*c* in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 302 may transition the lumens 326, 314 of the gas supply tubing 240*c* and the lens wash supply tubing 245*c* to a side-by-side arrangement. In some embodiments, the gas supply tubing 240*c* and the lens was supply tubing 245*c* may be coupled to the first inlet end 304 of the housing 302 in a side-by-side arrangement.

The housing 302 may define a first fluid lumen 308 extending from a first fluid inlet 310 to a first fluid outlet 312 and a second lumen 318 extending from a second fluid inlet 320 to a second fluid outlet 322. The first and second lumens 308, 318 may extend from or branch from a shared fluid lumen 316. The fluids traveling through the first and second lumens 308, 318 may be fluidly isolated from one another in the shared fluid lumen 316 via the gas/lens wash supply tubing 240*c*, 245*c*. For example, the lens wash supply tubing 245*c* may extend distally beyond the second fluid inlet 320 to fluidly isolate the first and second lumens 308, 318.

It is contemplated that a location of the first fluid inlet 310 may vary along a length of the housing 302 and may at least partially depend on a location of the second end 324 of the lens wash supply tubing 245*c*. The first fluid lumen 308 may be in fluid communication with a lumen 314 of the lens wash supply tubing 245*c* to supply lens wash fluid to the endoscope. Fluid may exit an opening of the lens wash supply tubing 245*c* at the second end 324 thereof and enter the first fluid lumen 308 of the housing 302. In some embodiments, a length of the lens wash supply tubing 245*c* may extend coaxially through the shared fluid lumen 316 such that the second end thereof is positioned between the first and second ends 304, 306 of the housing 302. In some embodiments, a diameter of the shared fluid lumen 316 may taper or reduce in diameter towards the second end 306 of the housing 302. An outer surface of the lens wash supply tubing 245*c* may frictionally engage an inner surface of the housing 302 defining the shared fluid lumen 316 and/or the first fluid lumen 308 adjacent a reduced diameter portion thereof. This may fluidly isolate the first fluid outlet 312 from the second fluid outlet 322.

A second end 328 of the gas supply tubing 240*c* may be disposed over an outer surface of the housing 302 adjacent the first end 304 thereof. For example, the second end 328 of the gas supply tubing 240*c* may be disposed over and frictionally engage a neck portion 330 of the housing 302 to provide a gas-tight coupling between the gas supply tubing 240*c* and the housing 302. In some embodiments, the housing 302 may include a radially extending protrusion or ridge 332 configured to provide a mechanical stop for the second end 328 of the gas supply tubing 240*c*. In other embodiments, the second end of the gas supply tubing 240*c* may be disposed and secured within the shared fluid lumen 316. The second fluid lumen 318 of the housing 302 may be in fluid communication with the lumen 326 of the gas supply tubing 240*c*. Air/gas may enter the second fluid lumen 318 via the second fluid inlet 320. The engagement of the outer surface of the lens wash supply tubing 245*c* and the inner surface of the housing 302 defining the shared fluid lumen 316 and/or the first fluid lumen 308 may prevent air/gas within the lumen 326 of the gas supply tubing 240*c* from entering the first fluid lumen 308 of the housing 302.

The housing 302 may further include a flow control mechanism 334 configured to selectively fluidly couple the first fluid outlet 312 with the first fluid inlet 310. While not explicitly shown, in some embodiments, a flow control mechanism may be provided within the second fluid lumen 318 to selectively couple the second fluid outlet 322 with the second fluid inlet 320. In some embodiments, the flow control mechanism 334 may be positioned adjacent to the first fluid outlet 312. However, this is not required. The flow control mechanism 334 may be positioned anywhere between the first fluid inlet 310 and the first fluid outlet 312, as desired. In the illustrated embodiment, the flow control mechanism 334 may be a septum 336 extending across an entirety of the cross-section of the first fluid lumen 308 or substantially across an entirety of the cross-section of the first fluid lumen 308. The septum 336 may be over molded with the housing 302. In some examples, the septum 336 may be formed as a unitary structure with an over molded cover 338 extending about an exterior of the housing 302 and extending at least partially within the first fluid lumen 308. In other examples, the septum 336 may be formed as a separate component and coupled to an interior of the housing 302. It is contemplated that the septum 336 and/or cover 338 may be formed from a flexible material, such as, but not limited to, thermoplastic elastomers or silicone. The material may be selected to allow the septum 336 to be temporarily deformed to deliver a flow of fluid through the septum 336 and return to an original configuration to prevent a flow of fluid through the septum 336.

It is contemplated that the septum 336 may be formed as a solid structure and thereafter an aperture 340 extending through a thickness of the septum 336 may be formed. The aperture 340 may provide a selective fluid path from the first fluid inlet 310 to first fluid outlet 312. In some cases, the aperture 340 may be formed by puncturing the septum 336 after the septum 336 has been formed. It is contemplated that the aperture 340 may be formed by puncturing the septum 336 from both sides simultaneously with two pins or may be formed by puncturing with a single pin from a single direction.

In some embodiments, a second side surface of the septum 336 may include a generally conically tapered surface 342. While not explicitly shown, a first side surface of the septum 336 may include a generally conically tapered surface. The septum 336 may have a uniform cross-sectional thickness or may take other shapes, as desired. A thickness of the septum 336 may gradually reduce towards a radial center of the septum 336. This may allow the aperture 340 to expand or open to allow fluid or water to selectively pass therethrough. In some examples, the aperture 340 may be forced open by the pressurized water flowing through the lens wash supply tubing 245*c* to allow fluid to pass from the first fluid inlet 310, through the first fluid lumen 308 along flow path 344, out the first fluid outlet 312 and into the connector portion 265. In this example, in the absence of pressurized water flow, the aperture 340 may reduce in size to effectively prevent any residual water that is in the lens wash supply tubing 245*c* and/or the housing 302 from flowing out of the first fluid outlet 312 whether the connector 300 is connected to the connector portion 265 or uncoupled from the connector portion 265 (e.g., to change endoscopes) without user intervention. In another example, a water post on the connector portion 265 (e.g., detachable gas/lens wash connection 290) may force the aperture 340 open when the connector 300 is assembled with the connector portion to allow a fluid to pass from the first fluid inlet 310, through the first fluid lumen 308, out the first fluid outlet 312 and into the connector portion 265. When the connector 300 is uncoupled from the connector portion 265, the aperture 340 may reduce in size to effectively prevent any residual water that is in the lens wash supply tubing 245*c* and/or the housing 302 from flowing out of the first fluid outlet 312 without user intervention.

Figure 4:
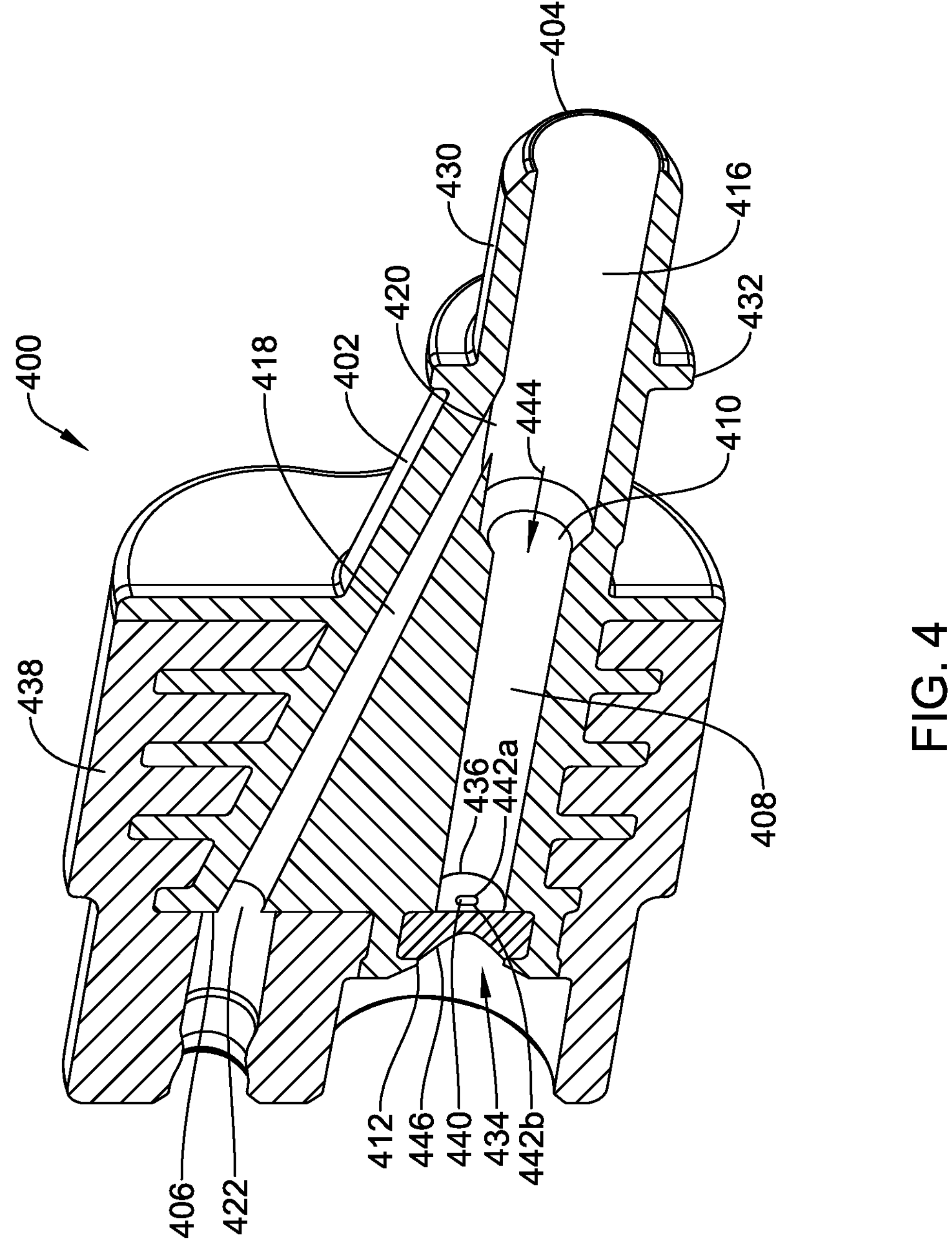
FIG. 4 depicts a cross-sectional view of another illustrative connector for connecting an endoscope end of the gas/lens wash supply tubing to the gas/lens wash connector on the connector portion.

FIG. 4 depicts a perspective cross-sectional view of another illustrative connector 400 for connecting an endoscope end of the gas/lens wash supply tubing 240*c*, 245*c* to the gas/lens wash connector 290 on the connector portion 265 (e.g., shown in FIG. 2). The connector 400 may include a housing 402 extending from a first inlet end 404 to a second outlet end 406. The first inlet end 404 may be configured to be coupled to the gas supply tubing and the lens wash supply tubing (not explicitly shown) and the second outlet end 406 may be configured to be coupled to the gas/lens wash connector on the connector portion. The gas supply tubing and lens wash supply tubing may be combined in a coaxial arrangement, as shown and described with respect to FIG. 3. For example, the gas supply tubing may define a lumen that is sufficiently large in diameter to encompass a smaller diameter lens wash supply tubing, coaxially received within the gas supply tubing, as well as provide air to the water source in an annular space surrounding the lens wash supply tubing to pressurize the water reservoir. The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 402 may transition the lumens of the gas supply tubing and the lens wash supply tubing to a side-by-side arrangement in a manner similar to that shown and described with respect to FIG. 3. In some embodiments, the gas supply tubing and the lens was supply tubing may be coupled to the first inlet end 404 of the housing 402 in a side-by-side arrangement.

The housing 402 may define a first fluid lumen 408 extending from a first fluid inlet 410 to a first fluid outlet 412 and a second fluid lumen 418 extending from a second fluid inlet 420 to a second fluid outlet 422. The first and second lumens 408, 418 may extend from or branch from a shared fluid lumen 416. The fluids traveling through the first and second lumens 408, 418 may be fluidly isolated from one another in the shared fluid lumen 416 via the gas/lens wash supply tubing in a manner similar to that described with respect to FIG. 3. For example, the lens wash supply tubing may extend distally beyond the second fluid inlet 420 to fluidly isolate the first and second lumens 408, 418 from one another.

It is contemplated that a location of the first fluid inlet 410 may vary along a length of the housing 402 and may at least partially depend on a location of the second end of the lens wash supply tubing. The first fluid lumen 408 may be in fluid communication with a lumen of the lens wash supply tubing to supply lens wash fluid to the endoscope. Fluid may exit an opening of the lens wash supply tubing at the second end thereof and enter the first fluid lumen 408 of the housing 402. In some embodiments, a length of the lens wash supply tubing may extend coaxially through the shared fluid lumen 416 such that the second end thereof is positioned between the first and second ends 404, 406 of the housing 402. In some embodiments, a diameter of the shared fluid lumen 416 may taper or reduce in diameter towards the second end 406 of the housing 402. An outer surface of the lens wash supply tubing may frictionally engage an inner surface of the housing 402 defining the shared fluid lumen 416 and/or the first fluid lumen 408 adjacent to a reduced diameter portion thereof. This may fluidly isolate the first fluid outlet 412 from the second fluid outlet 422.

A second end of the gas supply tubing may be disposed over an outer surface of the housing 402 adjacent the first end 404 thereof. For example, the second end of the gas supply tubing may be disposed over and frictionally engage a neck portion 430 of the housing 402 to provide a gas-tight coupling between the gas supply tubing and the housing 402. In some embodiments, the housing 402 may include a radially extending protrusion or ridge 432 configured to provide a mechanical stop for the second end of the gas supply tubing. In other embodiments, the second end of the gas supply tubing may be disposed and secured within the shared fluid lumen 416. The second fluid lumen 418 of the housing 402 may be in fluid communication with the lumen of the gas supply tubing. Air/gas may enter the second fluid lumen 418 via the second fluid inlet 420. The engagement of the outer surface of the lens wash supply tubing and the inner surface of the housing 402 defining the shared fluid lumen 416 and/or the first fluid lumen 408 may prevent air/gas within the lumen of the gas supply tubing from entering the first fluid lumen 408 of the housing 402.

The housing 402 may further include a flow control mechanism 434 configured to selectively fluidly couple the first fluid outlet 412 with the first fluid inlet 410. While not explicitly shown, in some embodiments, a flow control mechanism may be provided within the second fluid lumen 418 to selectively couple the second fluid outlet 422 with the second fluid inlet 420. In some embodiments, the flow control mechanism 434 may be positioned adjacent to the first fluid outlet 412. However, this is not required. The flow control mechanism 434 may be positioned anywhere between the first fluid inlet 410 and the first fluid outlet 412, as desired. In the illustrated embodiment, the flow control mechanism 434 may be a duckbill valve 436 extending across an entirety of the cross-section of the first fluid lumen 408 or substantially across an entirety of the cross-section of the first fluid lumen 408. The duckbill valve 436 may include two or more flaps 442*a*, 442*b* which are configured to move between a flattened closed configuration (shown in FIG. 4) and an opened configuration to allow fluid to pass through the duckbill valve 436 in a single direction. While the flow control mechanism 434 is shown and described as a duckbill valve 436, it is contemplated that other one-way valves or check valves may be used, as desired.

The duckbill valve 436 may be over molded with the housing 402. In some examples, the duckbill valve 436 may be formed as a unitary structure with an over molded cover 438 extending about an exterior of the housing 402 and extending at least partially within the first fluid lumen 408. In other examples, the duckbill valve 436 may be formed as a separate component and coupled to an interior of the housing 402. It is contemplated that the duckbill valve 436 and/or cover 438 may be formed from a flexible material, such as, but not limited to, thermoplastic elastomers or silicone. The material may be selected to allow the duckbill valve 436 to be temporarily deformed to deliver a flow of fluid through the duckbill valve 436 and return to an original configuration to prevent a flow of fluid through the duckbill valve 436.

The flaps 442*a*, 442*b* of the duckbill valve 436 may be configured to separate to define a fluid flow path 440 through the duckbill valve 436. The fluid flow path 440 may extend through a thickness of the duckbill valve 436 to selectively fluidly couple the first fluid inlet 410 with the first fluid outlet 412. It is contemplated that the flaps 442*a*, 442*b* may extend longitudinally in a direction generally parallel to a longitudinal axis of the first fluid lumen 408. In the illustrated embodiment, the flaps 442*a*, 442*b* may extend towards the second end 406 of the housing 402. This may allow the flaps 442*a*, 442*b* to open in response to a flow of fluid from the lens wash supply tube along flow path 444. For example, the flaps 442*a*, 442*b* may be forced open by the pressurized water flowing through the lens wash supply tubing to allow fluid to pass from the first fluid inlet 410, through the first fluid lumen 408, out the first fluid outlet 412, and into the connector portion 265. In this example, in the absence of pressurized water flow, the flaps 442*a*, 442*b* may close or come together to effectively prevent any residual water that is in the lens wash supply tubing and/or the housing 402 from flowing out of the first fluid outlet 412 whether the connector 400 is connected to the connector portion 265 or uncoupled from the connector portion (e.g., to change endoscopes), without user intervention.

In another example, the flaps 442*a*, 442*b* may extend towards the first end 404 of the housing 402. This may allow the water post on the connector portion (e.g., detachable gas/lens wash connection 290) to force the flaps 442*a*, 442*b* open when the connector 400 is assembled with the connector portion to allow a fluid to pass from the first fluid inlet 410, through the first fluid lumen 408, out the first fluid outlet 412 and into the connector portion 265. When the connector 400 is uncoupled from the connector portion 265, the flaps 442*a*, 442*b* may come or close to effectively prevent any residual water that is in the lens wash supply tubing 245*c* and/or the housing 402 from flowing out of the first fluid outlet 412, without user intervention.

In some embodiments, a second side surface of the duckbill valve 436 may include a generally conically tapered surface 446. For example, a thickness of the duckbill valve 436 may gradually reduce towards a radial center of the duckbill valve 436. However, this is not required. While not explicitly shown, a first side surface of the duckbill valve 436 may include a generally conically tapered surface. The duckbill valve 436 may have a uniform cross-sectional thickness or may take other shapes, as desired.

Figure 5A:
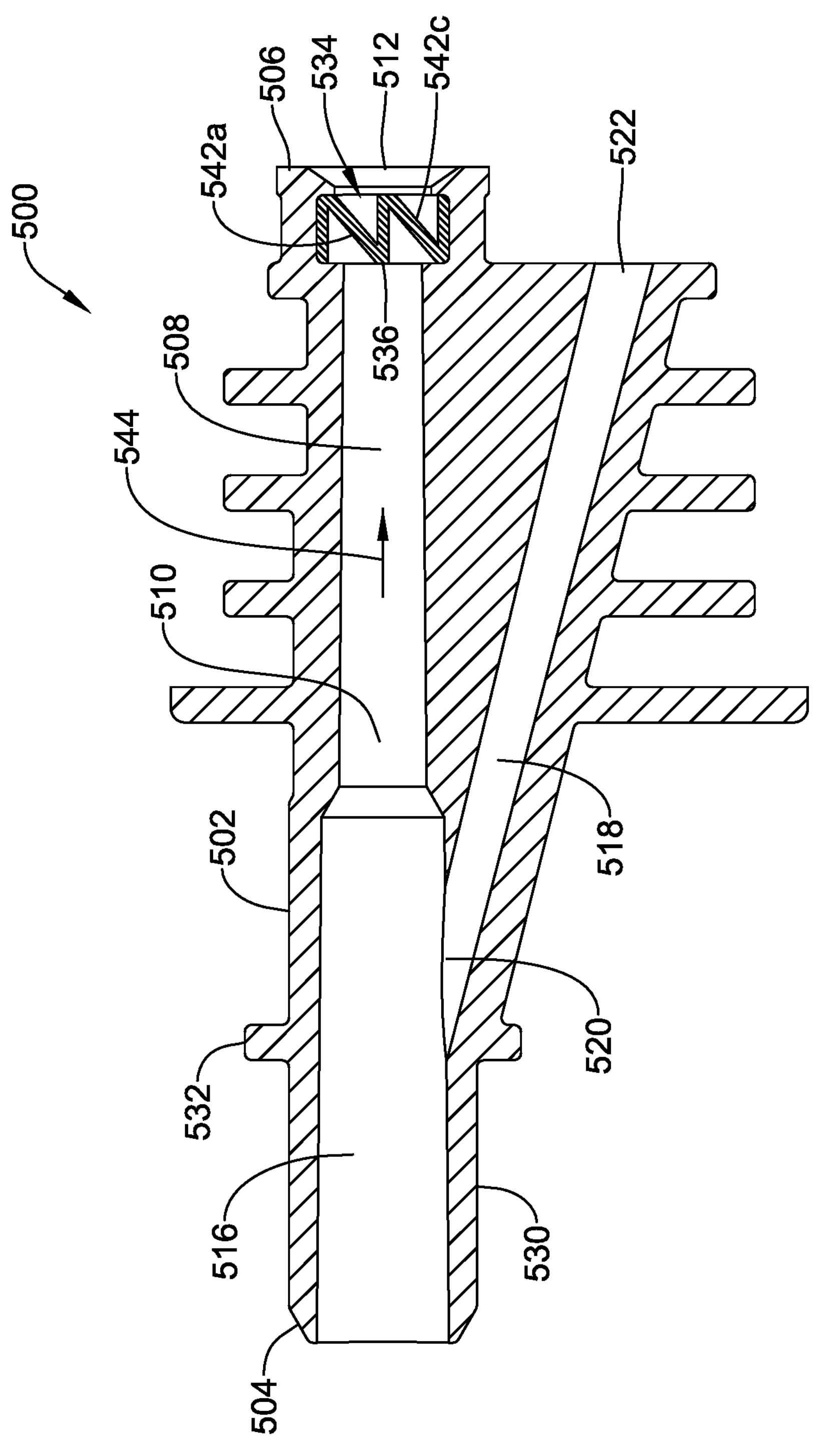
FIG. 5A depicts a cross-sectional view of another illustrative connector for connecting an endoscope end of the gas/lens wash supply tubing to the gas/lens wash connector on the connector portion.

FIG. 5A depicts a perspective cross-sectional view of another illustrative connector 500 for connecting an endoscope end of the gas/lens wash supply tubing 240*c*, 245*c* to the gas/lens wash connector 290 on the connector portion 265 (e.g., shown in FIG. 2). The connector 500 may include a housing 502 extending from a first inlet end 504 to a second outlet end 506. The first inlet end 504 may be configured to be coupled to the gas supply tubing and the lens wash supply tubing (not explicitly shown) and the second outlet end 506 may be configured to be coupled to the gas/lens wash connector on the connector portion. The gas supply tubing and lens wash supply tubing may be combined in a coaxial arrangement, as shown and described with respect to FIG. 3. For example, the gas supply tubing may define a lumen that is sufficiently large in diameter to encompass a smaller diameter lens wash supply tubing, coaxially received within the gas supply tubing, as well as provide air to the water source in an annular space surrounding the lens wash supply tubing to pressurize the water reservoir. The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 502 may transition the lumens of the gas supply tubing and the lens wash supply tubing to a side-by-side arrangement in a manner similar to that shown and described with respect to FIG. 3. In some embodiments, the gas supply tubing and the lens was supply tubing may be coupled to the first inlet end 504 of the housing 502 in a side-by-side arrangement.

The housing 502 may define a first fluid lumen 508 extending from a first fluid inlet 510 to a first fluid outlet 512 and a second fluid lumen 518 extending from a second fluid inlet 520 to a second fluid outlet 522. The first and second lumens 508, 518 may extend from or branch from a shared fluid lumen 516. The fluids traveling through the first and second lumens 508, 518 may be fluidly isolated from one another in the shared fluid lumen 516 via the gas/lens wash supply tubing in a manner similar to that described with respect to FIG. 3. For example, the lens wash supply tubing may extend distally beyond the second fluid inlet 520 to fluidly isolate the first and second lumens 508, 518 from one another.

It is contemplated that a location of the first fluid inlet 510 may vary along a length of the housing 502 and may at least partially depend on a location of the second end of the lens wash supply tubing. The first fluid lumen 508 may be in fluid the endoscope. Fluid may exit an opening of the lens wash supply tubing at the second end thereof and enter the first fluid lumen 508 of the housing 502. In some embodiments, a length of the lens wash supply tubing may extend coaxially through the shared fluid lumen 516 such that the second end thereof is positioned between the first and second ends 504, 506 of the housing 502. In some embodiments, a diameter of the shared fluid lumen 516 may taper or reduce in diameter towards the second end 506 of the housing 502. An outer surface of the lens wash supply tubing may frictionally engage an inner surface of the housing 502 defining the shared fluid lumen 516 and/or the first fluid lumen 508 adjacent to a reduced diameter portion thereof. This may fluidly isolate the first fluid outlet 512 from the second fluid outlet 522.

A second end of the gas supply tubing may be disposed over an outer surface of the housing 502 adjacent the first end 504 thereof. For example, the second end of the gas supply tubing may be disposed over and frictionally engage a neck portion 530 of the housing 502 to provide a gas-tight coupling between the gas supply tubing and the housing 502. In some embodiments, the housing 502 may include a radially extending protrusion or ridge 532 configured to provide a mechanical stop for the second end of the gas supply tubing. In other embodiments, the second end of the gas supply tubing may be disposed and secured within the shared fluid lumen 516. The second fluid lumen 518 of the housing 502 may be in fluid communication with the lumen of the gas supply tubing. Air/gas may enter the second fluid lumen 518 via the second fluid inlet 520. The engagement of the outer surface of the lens wash supply tubing and the inner surface of the housing 502 defining the shared fluid lumen 516 and/or the first fluid lumen 508 may prevent air/gas within the lumen of the gas supply tubing from entering the first fluid lumen 508 of the housing 502.

The housing 502 may further include a flow control mechanism 534 configured to selectively fluidly couple the first fluid outlet 512 with the first fluid inlet 510. In some embodiments, the flow control mechanism 534 may be positioned adjacent to the first fluid outlet 512. However, this is not required. The flow control mechanism 534 may be positioned anywhere between the first fluid inlet 510 and the first fluid outlet 512, as desired. In the illustrated embodiment, the flow control mechanism 534 may be an iris valve 536 extending across an entirety of the cross-section of the first fluid lumen 508 or substantially across an entirety of the cross-section of the first fluid lumen 508. Referring additionally to FIG. 5B which illustrates an end view of the illustrative iris valve 536 in a closed configuration, the iris valve 536 may include a plurality of flaps 542*a-e* which are configured to move between a closed configuration (shown in FIGS. 5A and 5B) and an opened configuration to allow fluid to pass through the iris valve 536. While the flow control mechanism 534 is shown and described as an iris valve 536, it is contemplated that other one-way valves or check valves may be used, as desired.

The flaps 542*a-e* may extend radially inwards from a retaining ring 546. In some cases, the flaps 542*a-e* may overlap to completely block the first fluid lumen 508 when the iris valve 536 is in the closed configuration. In other embodiments, a small opening 548 may be present at the center of the iris valve 536 when the iris valve 536 is in the closed configuration. While the iris valve 536 is illustrated as including five flaps 542*a-e*, it is contemplated that the iris valve 536 may include fewer than five or more than five flaps, as desired. The flaps 542*a-e* may be formed from a flexible material, such as, but not limited to, thermoplastic elastomers or silicone. The material may be selected to allow the iris valve 536 to be temporarily deformed to deliver a flow of fluid through the iris valve 536 and return to an original configuration to prevent a flow of fluid through the iris valve 536.

The flaps 542*a-e* of the iris valve 536 may be configured to separate to define a fluid flow path 440 through the iris valve 536. The fluid flow path may extend through a thickness of the iris valve 536 to selectively fluidly couple the first fluid inlet 510 with the first fluid outlet 512. It is contemplated that the flaps 542*a-e* may be arranged to open towards the first inlet end 504 of the housing 502, towards the second outlet end 506 of the housing 502, or towards either end 504, 506 of the housing 502, as desired. For example, the flaps 542*a-e* may be arranged to allow the flaps 542*a-e* to open in response to a flow of fluid from the lens wash supply tube along flow path 544. For example, the flaps 542*a-e* may be forced open by the pressurized water flowing through the lens wash supply tubing to allow fluid to pass from the first fluid inlet 510, through the first fluid lumen 508, out the first fluid outlet 512, and into the connector portion 265. In this example, in the absence of pressurized water flow, the flaps 542*a-e* may close or come together to effectively prevent any residual water that is in the lens wash supply tubing and/or the housing 502 from flowing out of the first fluid outlet 512 whether the connector 500 is connected to the connector portion 265 or uncoupled from the connector portion (e.g., to change endoscopes), without user intervention.

Figure 5C:
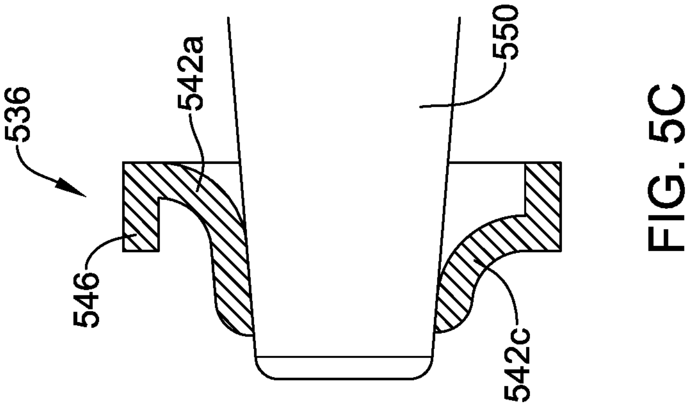
FIG. 5C depicts a cross-sectional view of an illustrative iris valve for use with the illustrative connector of FIG. 5A.
Figure 5B:
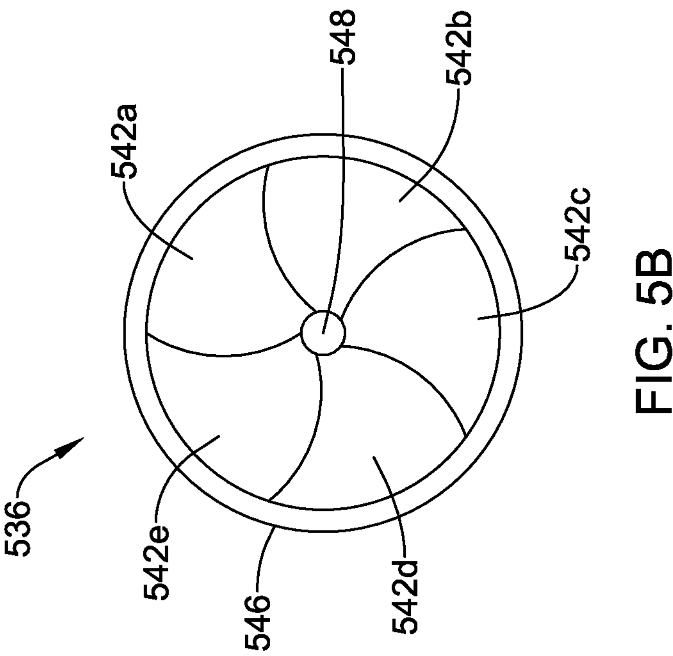
FIG. 5B depicts an end view of an illustrative iris valve for use with the illustrative connector of FIG. 5A

Referring additionally to FIG. 5C, which depicts a schematic partial cross-sectional view of the illustrative iris valve 536 assembled with a water post 550 on the connector portion 265, the flaps 542*a-e* may be arranged to allow the water post 550 (e.g., detachable gas/lens wash connection 290) to force the flaps 542*a-e* open when the connector 500 is assembled with the water post 550 of the connector portion to allow a fluid to pass from the first fluid inlet 510, through the first fluid lumen 508, out the first fluid outlet 512 and into the connector portion 265. When the connector 500 is uncoupled from the connector portion 265, the flaps 542*a-e* may come or close to effectively prevent any residual water that is in the lens wash supply tubing 245*c* and/or the housing 502 from flowing out of the first fluid outlet 512, without user intervention.

While not explicitly shown, in some examples, the connector 500 may include an over molded cover similar in form and function to the cover 338 described with respect to FIG. 3 extending about an exterior of the housing 502 and extending at least partially within the first fluid lumen 508. For example, all or parts of the iris valve 536 may be formed as a unitary structure with the cover, if so provided. In other examples, the iris valve 536 may be formed as a separate component and coupled to an interior of the housing 502.

Figure 6A:
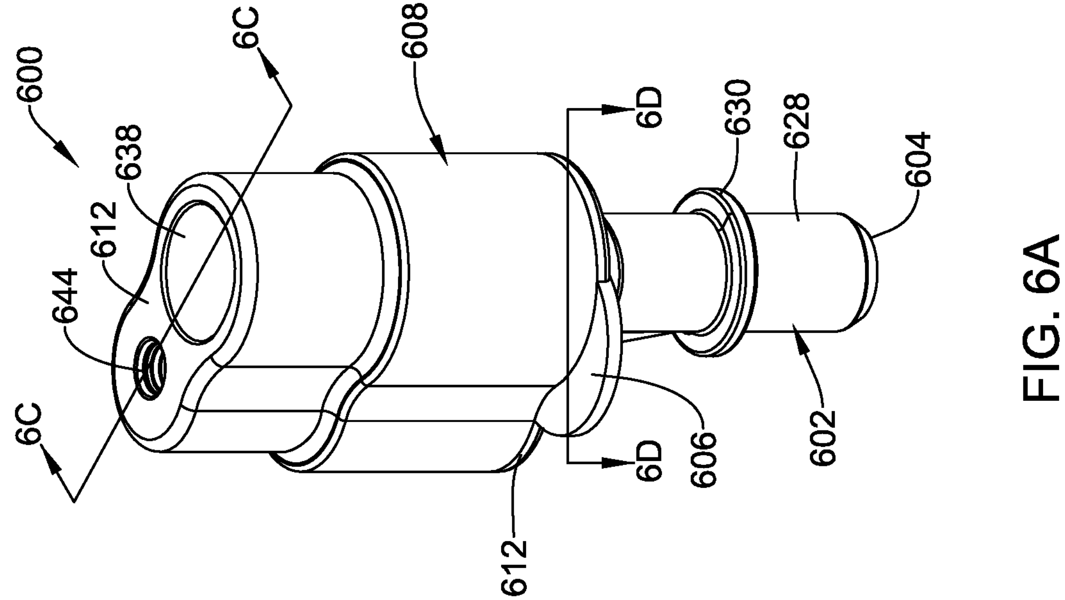
FIG. 6A depicts a perspective view of another illustrative connector for connecting an endoscope end of the gas/lens wash supply tubing to the gas/lens wash connector on the connector portion in a first configuration.
Figure 6B:
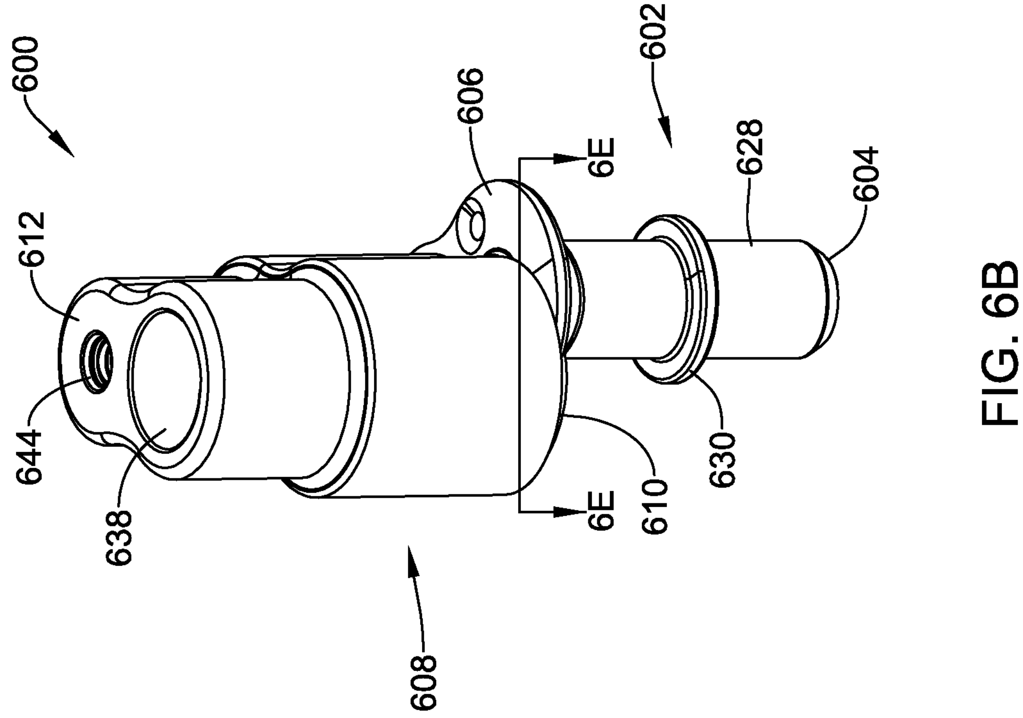
FIG. 6B depicts a perspective view the illustrative connector of FIG. 6A in a second configuration.

FIG. 6A depicts a perspective view of another illustrative connector 600 for connecting an endoscope end of the gas/lens wash supply tubing 240*c*, 245*c* to the gas/lens wash connector 290 on the connector portion 265 (e.g., shown in FIG. 2) in first configuration and FIG. 6B depicts a perspective view of the illustrative connector 600 in a second configuration. The connector 600 may include a first housing 602 extending from a first inlet end 604 to a second outlet end 606 and a second housing 608 extending from a first inlet end 610 to a second outlet end 612. The first inlet end 604 of the first housing 602 may be configured to be coupled to the gas supply tubing and the lens wash supply tubing (not explicitly shown) and the second outlet end 612 of the second housing 608 may be configured to be coupled to the gas/lens wash connector on the connector portion. The second outlet end 606 of the first housing 602 may be movably coupled to the first inlet end 610 of the second housing 608 to selectively couple fluid lumens with the first and second housings 602, 608, as will be described in more detail herein.

The gas supply tubing and lens wash supply tubing may be combined in a coaxial arrangement, as shown and described with respect to FIG. 3. For example, the gas supply tubing may define a lumen that is sufficiently large in diameter to encompass a smaller diameter lens wash supply tubing, coaxially received within the gas supply tubing, as well as provide air to the water source in an annular space surrounding the lens wash supply tubing to pressurize the water reservoir. The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 502 may transition the lumens of the gas supply tubing and the lens wash supply tubing to a side-by-side arrangement in a manner similar to that shown and described with respect to FIG. 3. In some embodiments, the gas supply tubing and the lens was supply tubing may be coupled to the first inlet end 604 of the first housing 602 in a side-by-side arrangement.

Figure 6C:
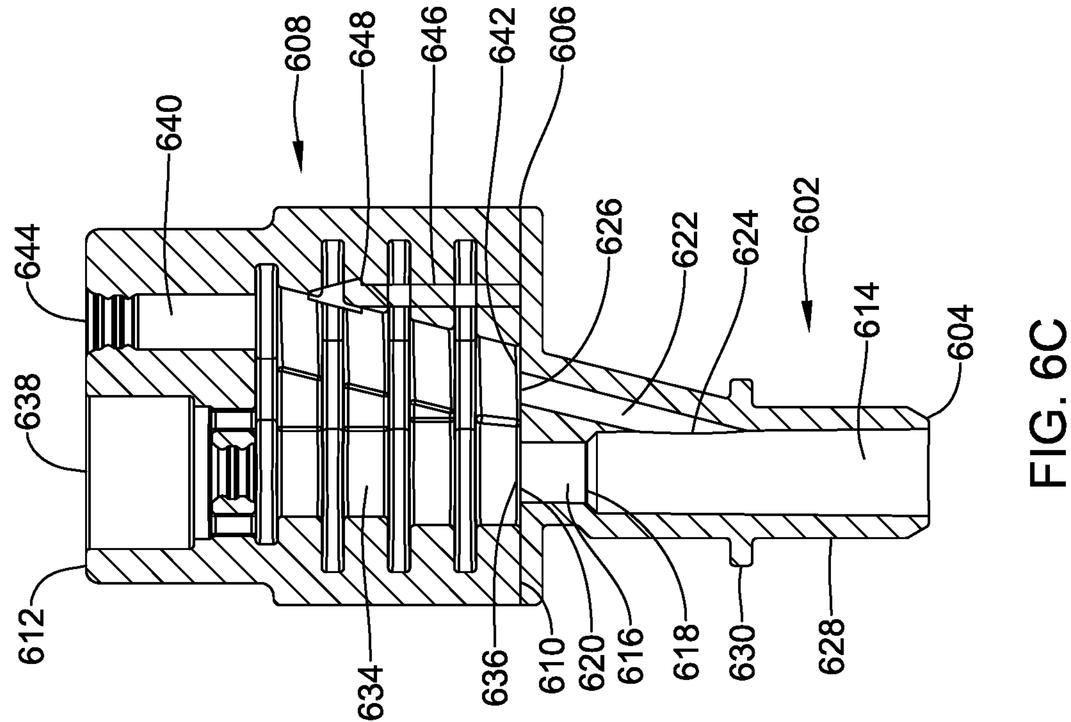
FIG. 6C depicts a schematic cross-sectional view of the illustrative connector of FIG. 6A, taken at line 6C-6C of FIG. 6A.

Referring additionally to FIG. 6C which depicts a schematic cross-sectional view of the illustrative connector 600, taken at line 6C-6C of FIG. 6A, the first housing 602 may define a first fluid lumen 616 extending from a first fluid inlet 618 to a first fluid outlet 620 and a second fluid lumen 622 extending from a second fluid inlet 624 to a second fluid outlet 626. The first and second lumens 616, 622 may extend from or branch from a shared fluid lumen 614. The fluids traveling through the first and second lumens 616, 622 may be fluidly isolated from one another in the shared fluid lumen 614 via the gas/lens wash supply tubing in a manner similar to that described with respect to FIG. 3. For example, the lens wash supply tubing may extend distally beyond the second fluid inlet 624 to fluidly isolate the first and second lumens 616, 622 from one another.

It is contemplated that a location of the first fluid inlet 618 may vary along a length of the first housing 602 and may at least partially depend on a location of the second end of the lens wash supply tubing. The first fluid lumen 616 may be in fluid the endoscope. Fluid may exit an opening of the lens wash supply tubing at the second end thereof and enter the first fluid lumen 616 of the first housing 602. In some embodiments, a length of the lens wash supply tubing may extend coaxially through the shared fluid lumen 614 such that the second end thereof is positioned between the first and second ends 604, 606 of the first housing 602. In some embodiments, a diameter of the shared fluid lumen 614 may taper or reduce in diameter towards the second end 606 of the first housing 602. An outer surface of the lens wash supply tubing may frictionally engage an inner surface of the first housing 602 defining the shared fluid lumen 614 and/or the first fluid lumen 616 adjacent to a reduced diameter portion thereof. This may fluidly isolate the first fluid outlet 620 from the second fluid outlet 626.

A second end of the gas supply tubing may be disposed over an outer surface of the first housing 602 adjacent the first end 604 thereof. For example, the second end of the gas supply tubing may be disposed over and frictionally engage a neck portion 628 of the first housing 602 to provide a gas-tight coupling between the gas supply tubing and the first housing 602. In some embodiments, the first housing 602 may include a radially extending protrusion or ridge 630 configured to provide a mechanical stop for the second end of the gas supply tubing. In other embodiments, the second end of the gas supply tubing 240 may be disposed and secured within the shared fluid lumen 614. The second fluid lumen 622 of the first housing 602 may be in fluid communication with the lumen of the gas supply tubing. Air/gas may enter the second fluid lumen 622 via the second fluid inlet 624. The engagement of the outer surface of the lens wash supply tubing and the inner surface of the first housing 602 defining the shared fluid lumen 614 and/or the first fluid lumen 616 may prevent air/gas within the lumen of the gas supply tubing from entering the first fluid lumen 616 of the first housing 602.

The second housing 608 may define a first fluid lumen 634 extending from a first fluid inlet 636 to a first fluid outlet 638 and a second fluid lumen 640 extending from a second fluid inlet 624 to a second fluid outlet 626. The first fluid inlet 636 of the second housing 608 may be configured to be selectively fluidly coupled with the first fluid outlet 620 of the first housing 602 to provide a flow of lens wash fluid from the lens wash supply tubing to the endoscope. The second fluid inlet 642 of the second housing 608 may be configured to be selectively fluidly coupled with the second fluid outlet 626 of the first housing 602 to provide a flow of air/gas to the endoscope and/or components thereof.

It is contemplated that the first housing 602 and the second housing 608 may be movably coupled to one another to selectively fluidly couple the first lumens 616, 634 and the second lumens 622, 640 thereof. For example, the first housing 602 and/or second housing 608 may slide, twist, or rotate relative to one another to selectively align the first lumens 616, 634 and the second lumens 622, 640 or misalign the first lumens 616, 634 and the second lumens 622, 640. FIG. 6A depicts the first and second housings 602, 608 in a first, aligned configuration. In this configuration, the first lumen 616 of the first housing 602 is in fluid communication with the first lumen 634 of the second housing 608 and the second lumen 622 of the first housing 602 is in fluid communication with the second lumen 640 of the second housing 608 to fluidly couple the gas supply tubing and the lens wash supply tubing with the connector portion and the endoscope. FIG. 6B depicts the first and second housings 602, 608 in a second, misaligned configuration. In this configuration, the first lumen 616 of the first housing 602 is fluidly isolated from the first lumen 634 of the second housing 608 and the second lumen 622 of the first housing 602 is fluidly isolated from the second lumen 640 of the second housing 608.

Returning to FIG. 6C, the first housing 602 may include a post 646 extending from the second end 606 thereof in a direction opposite the first end 604. The post 646 may be configured to be received within a mating aperture 650 (see, for example, FIGS. 6D and 6E) of the second housing 608. The post 646 may be configured to movably secure the first housing 602 and the second housing 608 to one another. The post 646 may include an enlarged anchor end 648 configured to engage a mating surface in the second housing 608. This mechanical engagement may allow the post 646 to be inserted into the mating aperture 650 while precluding unintentional disassembly of the post 646 from the aperture 650. In the illustrated embodiment, the anchor end 648 has generally conical arrow like shape, the anchor end 648 may take any shape desired. It is further contemplated that the anchor end 648 need not be enlarged relative to the remainder of the post 646.

Figure 6E:
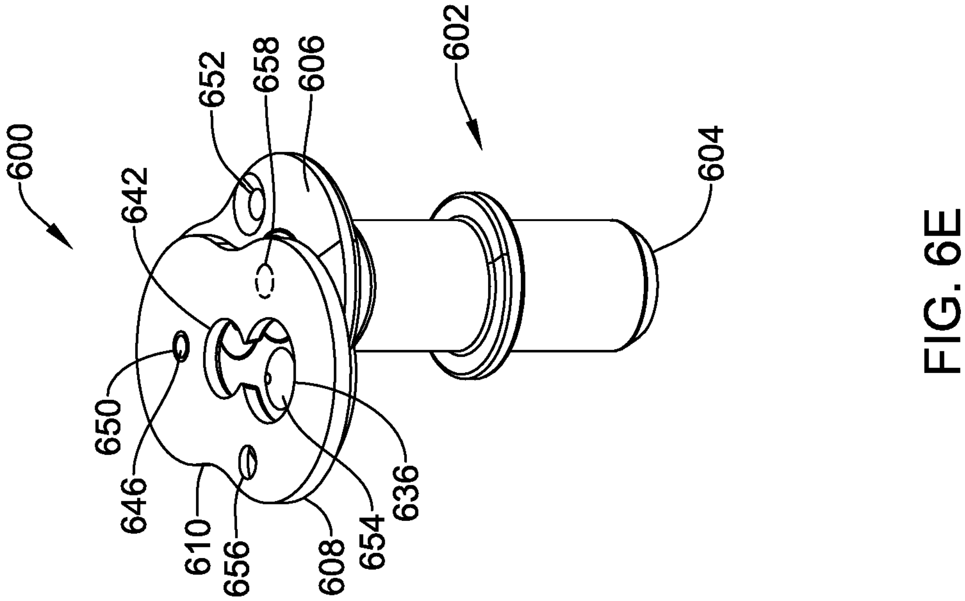
FIG. 6E depicts a partial cross-sectional view of the connector of FIG. 6B taken at line 6E-6E of FIG. 6B.
Figure 6D:
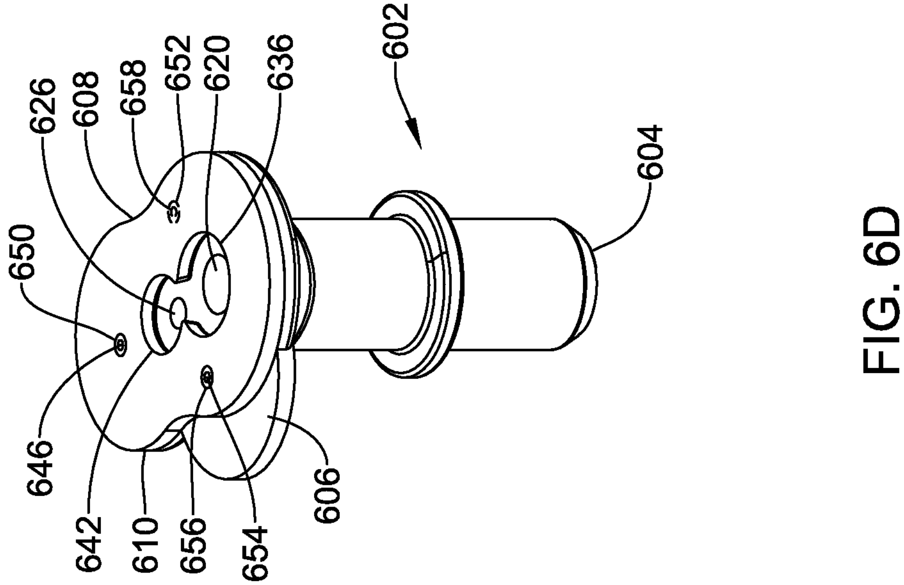
FIG. 6D depicts a partial cross-sectional view of the connector of FIG. 6A taken at line 6D-6D of FIG. 6A.

The first and second housings 602, 608 may include features which temporarily secure the housings 602, 608 in a desired configuration and/or alert the user that the correct positioning has been obtained. FIG. 6D depicts a partial cross-sectional view of the connector 600 taken at line 6D-6D of FIG. 6A and FIG. 6E depicts a partial cross-sectional view of the connector 600 taken at line 6E-6E of FIG. 6B. The first housing 602 may include a first recess 652 formed in the second end 606 thereof and a first protrusion 654 extending from the second end 606 (in a direction away from the first end 604). The second housing 608 may include a second recess 656 formed in the first end 610 thereof and a second protrusion 658 extending from the first end 610 (in a direction away from the second end 612). The first protrusion 654 of the first housing 602 may be configured to selectively engage the second recess 656 of the second housing 608 or the first fluid inlet 636 of the second housing 608. Further, the second protrusion 658 of the second housing 608 may be configured to selectively engage the first recess 652 of the first hosing or the first fluid outlet 620 of the first housing 602. For example, when the first and second housings 602, 608 are in the first configuration configured to fluidly couple the gas/lens wash supply tubing with the connector portion via the connector 600, as shown in FIG. 6D, the first protrusion 654 of the first housing 602 may engage the second recess 656 of the second housing 608 and the second protrusion 658 of the second housing 608 may engage the first recess 652 of the first housing 602. When the first and second housings 602, 608 are in the second configuration configured to fluidly isolate the gas/lens wash supply tubing from the second housing 608, as shown in FIG. 6E, the first protrusion 654 of the first housing 602 may engage the first fluid inlet 636 of the second housing 608 and the second protrusion 658 of the second housing 608 may engage the first fluid outlet 620 of the first housing 602. It is contemplated that moving the connector 600 to misalign the first fluid lumens 616, 634 and the second fluid lumens 622, 640 of the first and second housings 602, 608 may position a solid body portion of the second housing 608 over the first and second fluid outlets 620, 626 of the first housing 602. Such positioning may prevent fluid from the lens wash supply tubing from leaking from or dripping from the first and/or second outlets 620, 626 when the connector 600 is uncoupled from the endoscope. It is contemplated that the protrusions 654, 658 and recesses 652, 656 may provide the user with tactile or audible feedback indicating that the desired relative orientation of the first and second housings 602, 608 has been obtained. It is further contemplated that the protrusions 654, 658 and recesses 652,656 may be positioned to ensure that the first and second housings 602, 608 are in the proper configuration to allow air/gas and lens wash to flow into the endoscope.

In some embodiments, one or both of the first or second housings 602, 608 may be formed from a flexible or deformable material, such as, but not limited to, thermoplastic elastomers or silicone. It is contemplated that forming at least one of the first or second housings 602, 608 from a deformable or flexible material may allow a fluid or gas-tight seal to occur when the first and second housings 602, 608 are in the misaligned configuration. It is further contemplated that that forming at least one of the first or second housings 602, 608 from a deformable or flexible material may facilitate actuation of the first or second housing 602, 608 to move between the aligned and misaligned configurations.

Figure 7B:
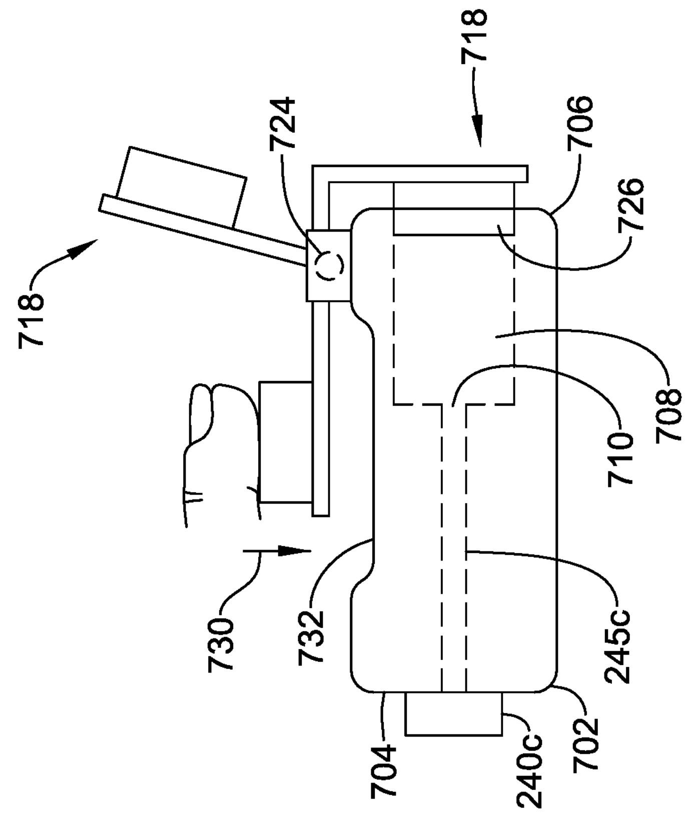
FIG. 7B depicts a side view the illustrative connector of FIG. 7A in a second configuration.
Figure 7A:
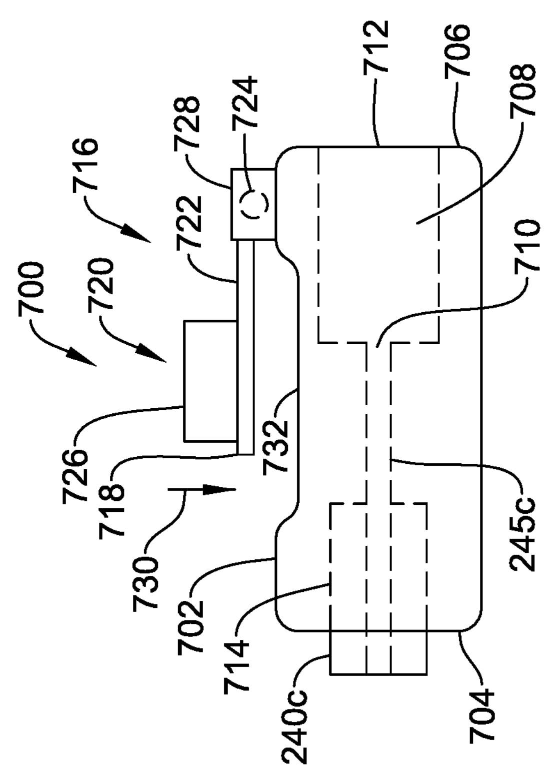
FIG. 7A depicts a side view of another illustrative connector for connecting an endoscope end of the gas/lens wash supply tubing to the gas/lens wash connector on the connector portion in a first configuration.

FIG. 7A depicts a schematic side view of another illustrative connector 700 for connecting an endoscope end of the gas/lens wash supply tubing 240*c*, 245*c* to the gas/lens wash connector 290 on the connector portion 265 (e.g., shown in FIG. 2) in a first configuration. FIG. 7B depicts a schematic side view of the illustrative connector 700 of FIG. 7A in a second configuration. The connector 700 may include a housing 702 extending from a first inlet end 704 to a second outlet end 706. The first inlet end 704 may be configured to be coupled to the gas supply tubing 240*c* and the lens wash supply tubing 245*c* and the second outlet end 706 may be configured to be coupled to the gas/lens wash connector on the connector portion. The gas supply tubing 240*c* and lens wash supply tubing 245*c* may be combined in a coaxial arrangement, as shown and described with respect to FIG. 3. For example, the gas supply tubing 240*c* may define a lumen that is sufficiently large in diameter to encompass a smaller diameter lens wash supply tubing 245*c*, coaxially received within the gas supply tubing 240*c*, as well as provide air to the water source in an annular space surrounding the lens wash supply tubing 245*c* to pressurize the water reservoir. The lens wash supply tubing 245*c* may be configured to exit the lumen defined by the coaxial gas supply tubing 240*c* in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 702 may transition the lumens of the gas supply tubing and the lens wash supply tubing to a side-by-side arrangement in a manner similar to that shown and described with respect to FIG. 3. In some embodiments, the gas supply tubing and the lens was supply tubing may be coupled to the first inlet end 704 of the housing 702 in a side-by-side arrangement.

The housing 702 may define a first fluid lumen 708 extending from a first fluid inlet 710 to a first fluid outlet 712 and a second fluid lumen (not explicitly shown) extending from a second fluid inlet to a second fluid outlet. The first lumen 708 and the second lumen may extend from or branch from a shared fluid lumen 714. It is contemplated that the arrangement of the first, second, and shared fluid lumens 708, 714 may be similar to that described with respect to FIG. 3. The fluids traveling through the first lumen and second lumen may be fluidly isolated from one another in the shared fluid lumen 714 via the gas/lens wash supply tubing in a manner similar to that described with respect to FIG. 3. For example, the lens wash supply tubing may extend distally beyond the second fluid inlet to fluidly isolate the first lumen 708 and the second lumen from one another.

It is contemplated that a location of the first fluid inlet 710 may vary along a length of the housing 702 and may at least partially depend on a location of the second end of the lens wash supply tubing 245*c*. The first fluid lumen 708 may be in fluid communication with a lumen of the lens wash supply tubing 245*c* to supply lens wash fluid to the endoscope. Fluid may exit an opening of the lens wash supply tubing 245*c* at the second end thereof and enter the first fluid lumen 708 of the housing 702. In some embodiments, a length of the lens wash supply tubing 245*c* may extend coaxially through the shared fluid lumen 714 such that the second end thereof is positioned between the first and second ends 704, 706 of the housing 702. In some embodiments, a diameter of the shared fluid lumen 714 may taper or reduce in diameter towards the second end 706 of the housing 702. An outer surface of the lens wash supply tubing 245*c* may frictionally engage an inner surface of the housing 702 defining the shared fluid lumen 714 and/or the first fluid lumen 708 adjacent to a reduced diameter portion thereof. This may fluidly isolate the first fluid outlet 712 from the second fluid outlet.

A second end of the gas supply tubing 240*c* may be disposed over an outer surface of the housing 702 adjacent the first end 704 thereof. For example, the second end of the gas supply tubing may be disposed over and frictionally engage a neck portion of the housing 702 to provide a gas-tight coupling between the gas supply tubing and the housing 702. In some embodiments, the housing 702 may include a radially extending protrusion or ridge configured to provide a mechanical stop for the second end of the gas supply tubing. In other embodiments, the second end of the gas supply tubing 240*c* may be disposed and secured within the shared fluid lumen 714. The second fluid lumen of the housing 702 may be in fluid communication with the lumen of the gas supply tubing 240*c*. Air/gas may enter the second fluid lumen via the second fluid inlet. The engagement of the outer surface of the lens wash supply tubing 245*c* and the inner surface of the housing 702 defining the shared fluid lumen 714 and/or the first fluid lumen 708 may prevent air/gas within the lumen of the gas supply tubing 240*c* from entering the first fluid lumen 708 of the housing 702.

The housing 702 may further include a flow control mechanism 716 configured to selectively fluidly couple the first fluid outlet 712 with the first fluid inlet 710. While not explicitly shown, in some embodiments, a flow control mechanism may be provided within the second fluid lumen to selectively couple the second fluid outlet with the second fluid inlet. In some embodiments, the flow control mechanism 716 may be positioned adjacent to the first fluid outlet 712. However, this is not required. In the illustrated embodiment, the flow control mechanism 716 may be an actuatable cap, such as, but not limited to, a spring-loaded cap assembly 718. While the assembly 718 is shown and described as spring-loaded, it is contemplated that other actuation mechanisms may be used as desired, including, but not limited to, manual actuation, buttons, switches, etc. The spring-loaded cap assembly 718 may include a cap member 720 and an arm 722. The arm 722 may be coupled to rotatable hinge 724 configured to allow the spring-loaded cap assembly 718 to move between an open configuration (as shown in FIG. 7A configured to allow fluid to exit the first fluid outlet 712 and a closed configuration (as shown in FIG. 7B) configured to prevent fluid from exiting the first fluid outlet 712. The cap member 720 may include a sealing portion 726. The sealing portion 726 may be formed from a flexible material, such as, but not limited to, thermoplastic elastomers or silicone. The sealing portion 726 may be configured to form a fluid-tight seal with the first fluid outlet 712. In some cases, the sealing portion 726 may extend at least partially into the first fluid lumen 708. In other examples, the sealing portion 726 may be disposed over an entirety of the first fluid outlet 712.

The spring-loaded cap assembly 718 may be held in the open configuration with a latch mechanism 728. The latch mechanism 728 may be biased to the locked configuration using, for example, a spring mechanism. The latch mechanism 728 may be temporarily moved to an unlocked configuration by a downward pressure on the cap member 720, as shown at arrow 730. This may allow the latch mechanism 728 to temporarily unlock and engage a mating feature on the arm 722 to hold the spring-loaded cap assembly 718 in the open configuration. When it is desired to close the first fluid outlet 712, a downward force 730 may be applied to the cap member 720, as shown in FIG. 7B. This may release the latch mechanism 728 from the arm 722. Upon release of the latch mechanism 728, the hinge 724 may move the spring-loaded cap assembly 718 to the closed configuration, as shown in FIG. 7B with the general motion of the spring-loaded cap assembly 718 shown in dashed lines in FIG. 7B. It is contemplated that the hinge 724 may include a biasing mechanism configured to bias the spring-loaded cap assembly 718 to the closed configuration. The user may overcome the bias of the hinge 724 to move the spring-loaded cap assembly 718 to the open configuration and the latch mechanism 728 may hold the spring-loaded cap assembly 718 in the open configuration until the user actuates the cap member 720.

Figures 8A, 8B:
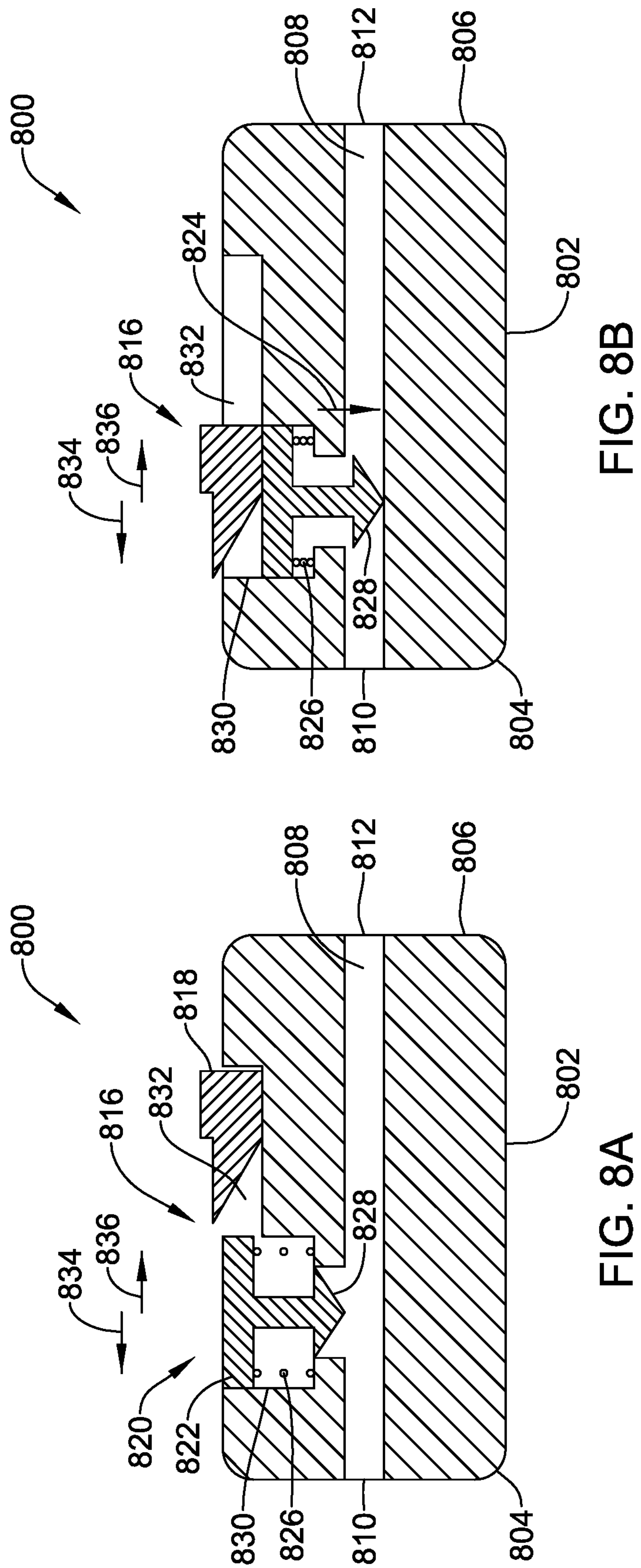
FIG. 8A depicts a cross-sectional view of another illustrative connector for connecting an endoscope end of the gas/lens wash supply tubing to the gas/lens wash connector on the connector portion in a first configuration.
FIG. 8B depicts a cross-sectional view the illustrative connector of FIG. 8A in a second configuration.

FIG. 8A depicts a schematic cross-sectional view of another illustrative connector 800 for connecting an endoscope end of the gas/lens wash supply tubing 240*c*, 245*c* to the gas/lens wash connector 290 on the connector portion 265 (e.g., shown in FIG. 2) in a first configuration. FIG. 8B depicts a schematic cross-sectional view of the illustrative connector 800 of FIG. 7A in a second configuration. The connector 800 may include a housing 802 extending from a first inlet end 804 to a second outlet end 806. The first inlet end 804 may be configured to be coupled to the gas supply tubing and the lens wash supply tubing and the second outlet end 806 may be configured to be coupled to the gas/lens wash connector on the connector portion. The gas supply tubing and lens wash supply tubing may be combined in a coaxial arrangement, as shown and described with respect to FIG. 3. For example, the gas supply tubing may define a lumen that is sufficiently large in diameter to encompass a smaller diameter lens wash supply tubing, coaxially received within the gas supply, as well as provide air to the water source in an annular space surrounding the lens wash supply tubing to pressurize the water reservoir. The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2). In the illustrated embodiment, the housing 802 may transition the lumens of the gas supply tubing and the lens wash supply tubing to a side-by-side arrangement in a manner similar to that shown and described with respect to FIG. 3. In some embodiments, the gas supply tubing and the lens was supply tubing may be coupled to the first inlet end 804 of the housing 802 in a side-by-side arrangement.

The housing 802 may define a first fluid lumen 808 extending from a first fluid inlet 810 to a first fluid outlet 812 and a second fluid lumen (not explicitly shown) extending from a second fluid inlet to a second fluid outlet. The first lumen 808 and the second lumen may extend from or branch from a shared fluid lumen (not explicitly shown). It is contemplated that the arrangement of the first, second, and shared fluid lumens may be similar to that described with respect to FIG. 3. The fluids traveling through the first lumen and second lumen may be fluidly isolated from one another in the shared fluid lumen via the gas/lens wash supply tubing in a manner similar to that described with respect to FIG. 3. For example, the lens wash supply tubing may extend distally beyond the second fluid inlet to fluidly isolate the first lumen 808 and the second lumen from one another.

It is contemplated that a location of the first fluid inlet 810 may vary along a length of the housing 802 and may at least partially depend on a location of the second end of the lens wash supply tubing. The first fluid lumen 808 may be in fluid the endoscope. Fluid may exit an opening of the lens wash supply tubing at the second end thereof and enter the first fluid lumen 808 of the housing 802. In some embodiments, a length of the lens wash supply tubing may extend coaxially through the shared fluid lumen such that the second end thereof is positioned between the first and second ends 804, 806 of the housing 802. In some embodiments, a diameter of the shared fluid lumen may taper or reduce in diameter towards the second end 806 of the housing 802. An outer surface of the lens wash supply tubing may frictionally engage an inner surface of the housing 802 defining the shared fluid lumen and/or the first fluid lumen 808 adjacent to a reduced diameter portion thereof. This may fluidly isolate the first fluid outlet 812 from the second fluid outlet.

A second end of the gas supply tubing may be disposed over an outer surface of the housing 802 adjacent the first end 804 thereof. For example, the second end of the gas supply tubing may be disposed over and frictionally engage a neck portion of the housing 802 to provide a gas-tight coupling between the gas supply tubing and the housing 802. In some embodiments, the housing 802 may include a radially extending protrusion or ridge configured to provide a mechanical stop for the second end of the gas supply tubing. In other embodiments, the second end of the gas supply tubing may be disposed and secured within the shared fluid lumen. The second fluid lumen of the housing 802 may be in fluid communication with the lumen of the gas supply tubing. Air/gas may enter the second fluid lumen via the second fluid inlet. The engagement of the outer surface of the lens wash supply tubing and the inner surface of the housing 802 defining the shared fluid lumen and/or the first fluid lumen 808 may prevent air/gas within the lumen of the gas supply tubing from entering the first fluid lumen 808 of the housing 802.

The housing 802 may further include a flow control mechanism 816 configured to selectively fluidly couple the first fluid outlet 812 with the first fluid inlet 810. While not explicitly shown, in some embodiments, a flow control mechanism may be provided within the second fluid lumen to selectively couple the second fluid outlet with the second fluid inlet. In some embodiments, the flow control mechanism 816 may be positioned adjacent to the first fluid outlet 812. However, this is not required. The flow control mechanism 816 may be positioned anywhere between the first fluid inlet 810 and the first fluid outlet 812, as desired. Generally, the flow control mechanism 816 may include a slidable cam or actuation mechanism 818 configured to actuate a sealing member 820 to selectively allow a flow of fluid through the first fluid lumen 808 and out of the first fluid outlet 812.

The housing 802 may house a biasing mechanism, such as, but not limited to, a spring 826 and a positioning mechanism 822. The positioning mechanism 822 may be actuated via the actuation mechanism 818 to selectively compress the spring 826 to retract or advance the sealing member 820, as shown at arrow 824 in FIG. 8B. The positioning mechanism 822 may include a multi-stop positioning mechanism which may function in a manner similar to a retractable pen. While the actuation mechanism 818 is illustrated as longitudinally displaced in the closed configuration (FIG. 8B) relative to the open configuration (FIG. 8A), in some embodiments, the actuation mechanism 818 may return to a "home" position (as shown in FIG. 8A) after the positioning mechanism 822 has been moved.

The sealing member 820 may include a post 828 that is configured to be selectively disposed within the first fluid lumen 808 to selectively allow a flow of fluid from the first inlet opening 810 to the first outlet opening 812. The post 828 may be movable within an aperture 830 in the housing 802. The aperture 830 may extend generally orthogonal to the first fluid lumen 808. The post 828 may be sized and shaped to block or substantially block a flow of fluid from the first fluid inlet 810 to the first fluid outlet 812. It is contemplated that the post 828 may take any shape desired. The positioning mechanism 822 may have a cross-section that is greater than a cross-section of the aperture 830 to prevent fluid from exiting the first fluid lumen 808 via the aperture 830. It is contemplated that either or both of the housing 802 or the post 828 may be formed from a flexible material, such as, but not limited to, thermoplastic elastomers or silicone to facilitate the formation of a fluid-tight seal within the first fluid lumen 808.

To move the sealing member 820 between the open configuration (FIG. 8A) which allows fluid to flow from the first fluid inlet 810 to the first fluid outlet 812 and the closed configuration (FIG. 8B) which prevents fluid from flowing from the first fluid inlet 810 to the first fluid outlet 812, the actuation mechanism 818 may be slid or moved within a slot 832 in the housing 802. The slot 832 may extend generally parallel to the first fluid lumen 808, although this is not required. Movement of the actuation mechanism 818 in a first direction 834 may cause the actuation mechanism 818 to engage the positioning mechanism 822 and bias the sealing member 820 towards the first fluid lumen 808, as shown at arrow 824. In some embodiments, the actuation member 818 may remain in contact with the positioning mechanism 822 to maintain the sealing member 820 in the closed configuration. In other embodiments, the sealing member 820 may be held in the closed configuration with a latch mechanism and the actuation mechanism may return to the "home" configuration. To move the sealing member 820 to the open configuration, the actuation mechanism 818 may be moved away from the positioning member 822 as shown at arrow 836. Alternatively, the actuation mechanism 818 may be "clicked" in a manner similar to a pen (or moved first in direction 834 and returned in direction 836 to the "home" position) to disengage the latch mechanism holding the sealing member 820 in the closed configuration. Once the actuation mechanism 818 has disengaged from the positioning member 822, the spring 826 may bias the sealing member 820 away from the first fluid lumen 808 to allow of a flow of fluid to pass therethrough.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

The invention claimed is:

1. A connector arranged and configured to couple a tube set to an endoscope, the connector comprising:

a housing, the housing comprising:

a first fluid inlet configured to couple with the tube set;

a second fluid inlet;

a first fluid outlet configured to couple with the endoscope and in selective fluid communication with the first fluid inlet;

a second fluid outlet in fluid communication with the second fluid inlet; and a flow control mechanism configured to selectively fluidly couple the first fluid outlet with the first fluid inlet, wherein in a first configuration the flow control mechanism prevents fluid flowing in the first fluid inlet from flowing out of the first fluid outlet and in a second configuration the flow control mechanism allows the fluid flowing in the first fluid inlet to flow out of the first fluid outlet.

2. The connector of claim 1, wherein the flow control mechanism comprises a septum.

3. The connector of claim 2, wherein the septum comprises a though hole extending through a thickness thereof.

4. The connector of claim 1, wherein the flow control mechanism comprises a valve.

5. The connector of claim 4, wherein the valve is a duckbill valve.

6. The connector of claim 1, wherein the flow control mechanism is over molded with the housing.

7. The connector of claim 1, wherein the flow control mechanism is configured to open at a predetermined minimum pressure.

8. The connector of claim 4, wherein the valve comprises an iris valve.

9. The connector of claim 8, wherein the iris valve is configured to open when the connector is connected to an endoscope and close when the connector is disconnected from the endoscope.

10. The connector of claim 1, wherein the flow control mechanism comprises a spring-loaded cap.

11. The connector of claim 1, wherein the flow control mechanism comprises a slidable cam.

12. The connector of claim 11, wherein when the slidable cam is in a first configuration, the first fluid outlet is fluidly isolated from the first fluid inlet and when the slidable cam is in a second configuration, the first fluid outlet is in fluid communication with the first fluid inlet.

13. A connector arranged and configured to couple a tube set to an endoscope, the connector comprising:

a housing, the housing comprising:

a first fluid inlet;

a second fluid inlet;

a first fluid outlet in selective fluid communication with the first fluid inlet;

a second fluid outlet in fluid communication with the second fluid inlet; and a flow control mechanism configured to selectively fluidly couple the first fluid outlet with the first fluid inlet;

wherein in response to the first fluid outlets being coupled to an endoscope, the flow control mechanism opens to fluidly connect the first fluid outlet and the first fluid inlet, and in response to the first fluid outlet being uncoupled from the endoscope, the flow control mechanism closes to fluidly isolate the first fluid outlet from the first fluid inlet.

14. The connector of claim 13, wherein the flow control mechanism is configured to selectively open at a predetermined minimum pressure.

15. The connector of claim 13, wherein the flow control mechanism is configured to automatically fluidly isolate the first fluid outlet from the first fluid inlet when the first fluid outlet is uncoupled from the endoscope.

* * * * *